US007082369B1

(12) United States Patent
Rubin et al.

(10) Patent No.: US 7,082,369 B1
(45) Date of Patent: Jul. 25, 2006

(54) DISTRIBUTED BIOHAZARD SURVEILLANCE SYSTEM AND APPARATUS FOR ADAPTIVE AEROSOL COLLECTION AND SYNCHRONIZED PARTICULATE SAMPLING

(75) Inventors: Stuart H. Rubin, San Diego, CA (US); Shu-Ching Chen, Miami, FL (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 138 days.

(21) Appl. No.: 10/850,004

(22) Filed: May 20, 2004

Related U.S. Application Data

(63) Continuation-in-part of application No. 10/849,451, filed on May 19, 2004, now Pat. No. 7,006,923.

(51) Int. Cl.
*G01N 21/85* (2006.01)

(52) U.S. Cl. .............................. 702/19; 702/22; 702/2

(58) Field of Classification Search .................... 702/2, 702/3, 19, 22, 24, 23, 25, 26, 49; 96/63; 73/863.01, 863.23
See application file for complete search history.

(56) References Cited

U.S. PATENT DOCUMENTS 4,390,869 A * 6/1983 Christen et al. ............ 340/632
5,469,369 A * 11/1995 Rose-Pehrsson et al. ..... 702/27
5,491,642 A * 2/1996 Wormell et al. .............. 702/49
5,594,544 A * 1/1997 Horiuchi et al. .............. 356/73
5,815,417 A * 9/1998 Orr et al. ........................ 703/5
5,832,411 A * 11/1998 Schatzmann et al. ......... 702/23
5,895,922 A 4/1999 Ho
6,084,510 A * 7/2000 Lemelson et al. ..... 340/539.13
6,266,428 B1 7/2001 Flanigan
6,317,080 B1 11/2001 Baxter
6,490,530 B1 12/2002 Wyatt
6,532,067 B1 3/2003 Chang et al.
6,574,561 B1 * 6/2003 Alexander et al. ............. 702/5
6,613,571 B1 9/2003 Cordery et al.
6,653,651 B1 * 11/2003 Meinhart et al. ........... 250/573
6,656,253 B1 12/2003 Willey et al.
6,664,550 B1 12/2003 Rader et al.
2001/0027388 A1 * 10/2001 Beverina et al. .............. 703/22
2003/0065409 A1 * 4/2003 Raeth et al. .................. 700/31
2004/0012491 A1 * 1/2004 Kulesz et al. ............... 340/506
2004/0015336 A1 * 1/2004 Kulesz et al. ................. 703/11

* cited by examiner

*Primary Examiner*—Donald McElheny, Jr.
(74) *Attorney, Agent, or Firm*—Andrew J. Cameron; Michael A. Kagan; Peter A. Lipovsky

(57) ABSTRACT

A distributed biohazard surveillance system including a plurality of robust miniaturized remote monitoring stations for the detection, localized analysis and reporting of a broad range of biohazards. The remote monitoring station may be adapted to identify many different biological particles and is not limited to particular predetermined biohazard profiles. It is centrally and dynamically reconfigurable and can be adapted to operate unattended in a remote location. The distributed system may be used to locate and report unsuspected sources of biohazards and to monitor the localized effects in real-time cooperation with a centralized data processing facility.

13 Claims, 5 Drawing Sheets

DISTRIBUTED BIOHAZARD SURVEILLANCE SYSTEM AND APPARATUS FOR ADAPTIVE AEROSOL COLLECTION AND SYNCHRONIZED PARTICULATE SAMPLING

CROSS REFERENCE TO RELATED APPLICATIONS

This application is a continuation-in-part of application Ser. No. 10/849,451, entitled "Distributed Biohazard Surveillance System and Apparatus for Adaptive Aerosol Collection and Particulate Sampling," Navy Case No. 83,657, filed on May 19, 2004 now U.S. Pat. No. 7,006,923, hereby incorporated by reference.

STATEMENT OF GOVERNMENT INTEREST

This invention (Navy Case No. 96395) was developed with funds from the United States Department of the Navy. Licensing inquiries may be directed to the Office of Patent Counsel. Space and Naval Warfare Systems Center, San Diego, Code 20012, San Diego, Calif., 92152: telephone (619)553-3001.

BACKGROUND OF THE INVENTION

1. Field of the Invention

This invention relates generally to biohazard surveillance systems and more particularly to an adaptive distributed system for the collection and sampling of hazardous particulates.

2. Description of the Related Art

The challenges we face from biological threat agents are increasing. While microbes continue to evolve and biotechnology becomes more powerful, the inherent hazards to humans, plants, and animals from infectious microorganisms are greatly increased by their intentional use by terrorists. The need for faster and better capabilities for warning, response, and cleanup was painfully evident in the case of a small-scale deployment of a noncontagious, naturally occurring anthrax pathogen. Terrorist use of other biological agents may result in far greater loss of life; agents that might be contagious or perhaps engineered for increased virulence and resistance to medical treatment. As microbes evolve and compete for survival, naturally emerging threats must also be quickly identified and distinguished from suspected terrorism. While the focus on bioterrorism is driven primarily by concerns about attacks on humans, attacks on livestock and/or crops can be just as devastating. A recent outbreak of foot-and-mouth disease in Great Britain demonstrates the devastating effect microbes can have on livestock and the consequent effect on food supply and economies. Rogue states have actively explored both animal and plant pathogens as weapons.

Lessons learned from the Persian Gulf War highlighted the need for biological warfare agent detectors and the subsequent solutions improved capability on the battlefield. However, other biological hazard ("biohazard") surveillance deficiencies were soon recognized in the aftermath of conflict. "Gulf War Syndrome" and other ailments suffered by military personnel revealed a need for compact diagnostic tools with integrated sample-processing and detection capabilities to quickly identify disease-causing agents on and off the battlefield. In 1998, a consolidated approach was begun (at the Army Medical Institute for Infectious Diseases) to develop medical diagnostic systems using a common platform for biohazard identification entitled "The Common Diagnostic Systems for Biological Threats and Endemic Infectious Diseases." Research encompassed development of rapid sample-processing methods, identification technologies, reagents and size reduction of laboratory analysis platforms.

In 2002, the Department of Defense (DoD) defined a new approach to a common medical test platform for identifying biological warfare agents and pathogens of operational concern. The Joint Biological Agent Identification and Diagnostic System (JBAIDS) exemplifies this approach. JBAIDS will be configured to support reliable, fast, and specific identification of biological agents from a variety of clinical specimens and environmental sources. JBAIDS will enhance force protection by providing commanders with information to determine actions to protect against and avoid contamination and to restore operations following an attack. JBAIDS information will aid medical personnel in determining appropriate treatment, effective preventive medical measures, and medical prophylaxis in response to the presence of biological agents. Required to combat the threat of biological attack faced by U.S. forces deployed worldwide, JBAIDS will also improve protection against endemic infectious diseases, thereby filling a need identified during the Persian Gulf War for a compact diagnostic identification tool. Today's global military mission, with ongoing operations in war-torn locations teeming with infectious diseases, demands a readily accessible, far-forward biological agent identification capability. This is critical to maintaining troop readiness, quickly determining patient treatment, disposition (for example, quarantine and medical evacuation), and protecting the homeland population from infections acquired by the military, from bioterrorism, and from emerging disease threats.

The DoD has addressed the biological threat in the context of the battlefield. However, biological threat reduction in the civilian population context is different. For example, the average civilian is not trained or equipped for response, the public health system is not supported with the kind of central command and control systems associated with the military, different requirements exist on sensitivity and different levels of tolerance for false positives and false negatives, and there is a need for dealing with a broader set of potential agents. Also, much higher sensitivity is required for Counter Terrorism (CT) detection, raising substantial technology challenges and the need to assess background interferences that may be more significant for low-level detection and monitoring schemes.

The urgent need for improved biohazard surveillance capability was also recognized and described for the first time in other Government agencies during this period. For example, the United States Postal Service has developed a Biohazard Detection System (BDS) using proven technology to implement early identification of anthrax. The BDS unit consists of an air-collection hood, a cabinet where the collection and analysis devices are housed, a local computer network connection, and a site controller (a networked computer). All BDS processes are automated. The equipment continuously collects air samples from mail canceling equipment while the canceling operation is underway. The air collection hood is installed over the canceling equipment at the very first pinch point in the mail processing operation where it absorbs and concentrates airborne particles into a sterile water base. This creates a liquid sample that is injected into a cartridge. An automated polymerase chain reaction (PCR) test is performed on the liquid sample using sophisticated DNA matching to detect the presence of anthrax (*Bacillus anthracis*). The test sample is compared to a template for the anthrax DNA sequence for a match. The system concentrates air samples for a one-hour period followed by the PCR test that takes approximately 30 minutes. The BDS is simultaneously concentrating particles for the next sample while the PCR test is performed for the previous sample. So while the first result requires approximately 1½ hours, subsequent results are obtained every hour. Upon detection of a DNA match, the BDS computer network conveys that information to the site controller computer. Local management is notified directly by on-site BDS personnel and also by multiple forms of electronic communication from the BDS site controller. The emergency action plan is activated, the facility's building alarm is sounded and everyone in the building is evacuated. Disadvantageously, the BDS is not adapted for identifying biohazards other than the anthrax spore.

Practitioners in the art have proposed various solutions to the sampling, detection, analysis, identification and reporting problems associated with the biohazard surveillance requirement. For example, in U.S. Pat. No. 5,895,922, Ho describes a process and apparatus for detection of viable and potentially hazardous biological particles that may be dispersed in an airstream. Ho teaches a method for directing each of the contained particles along a linear path through air, in a sequential manner, and sampling them for determination of their size, whether they are biological and viable, and whether they are present in concentrations greater than background levels. The particle size identifies the particles as respirable or not and the particles are characterized as biological and viable by subjecting each particle in turn, to 340 nm, ultraviolet laser light and looking for the emission of fluorescence, which is typically emitted from bacteria or bacterial spores. Fluorescence detected in the 400–540 nm range signals the presence of nicotinamide adenine dinucleotide hydrogen, which is indicative of biological activity or viability. Ho's apparatus is compact, and power-efficient because he uses a solid state, ultraviolet laser that is actuated only when the particle is passing the laser and only if it is deemed to be a biologically viable candidate, but it is disadvantageous for use in a remote automated surveillance station.

In U.S. Pat. No. 6,266,428, Flanigan discloses a system and method for remote detection of hazardous vapors and aerosols by means of two differential spectral signature spectra taken in the field of view at a low spectral resolution. A first linear discriminant optimized for the low spectral resolution is applied to the first spectrum to obtain a first response, and a hazardous cloud is detected automatically in accordance with the first response. A second differential spectral signature spectrum is taken in the field of view at a higher spectral resolution and a second linear discriminant optimized for the higher spectral resolution is applied to the second spectrum to obtain a second response, which is formed into a false-color image and displayed to an operator. The operator discriminates the hazardous cloud in accordance with the image. The first and second linear discriminants can be formed by linear programming. Flanigan's system is disadvantageous for use in a remote automated surveillance station.

In U.S. Pat. No. 6,317,080, Baxter discloses a method of tracking airborne substances including the steps of detecting the presence of one or more airborne substances and releasing a tracking balloon into the path of the one or more airborne substances, the tracking balloon having a transmission means and a global positioning means adapted to communicate the latitude and longitude coordinates of the tracking balloon whereby the latitude and longitude coordinates of the tracking balloon are representative of the latitude and longitude of the one or more airborne substances previously detected. Baxter neither considers nor suggests solutions to the remote automated surveillance problem.

In U.S. Pat. No. 6,490,530, Wyatt discloses an aerosol hazard classification and early warning network that includes a large number of remote detector and analysis units, which are deployed throughout a region under surveillance for a potentially hazardous aerosol intrusion. Such aerosol threats may originate from fires, volcanic eruptions, or overt releases of biological and chemical agents dispersed in aerosol form. Among the former are the characteristic toxic aerosols released during refinery fires or explosions. The latter biological agents include bacterial spores, lyophilized bacterial cells, and virus preparations, whereas chemical agents might include various forms of nerve gasses and other anti-personnel gasses such as mustard, all commonly deployed in aerosol form. Each detector station contains an aerosol handling unit that samples and transfers ambient aerosol particles one-at-a-time through a light scattering chamber where each such particle is constrained to pass through a fine laser beam producing, thereby, an outgoing scattered light wave. The scattering chamber contains a plurality of scattered light detectors arranged to accept light scattered into different angular locations. The signals detected at each detector position are processed by a corresponding digital signal processing chip with the resulting set of digitized signals being transferred to an on-board central processing unit (CPU). The CPU analyzes the set of light scattering signals and identifies or otherwise characterizes each particle. The classification data are then stored and, on preprogrammed command, telemetered to a remote "central station" by means of an on-board telemetry unit. The central station analyzes the sets of data received from all the detector stations and then instructs, as necessary, selected detector stations via telemetric means to change their sampling and telemetry rates. As soon as sufficient data are available, the central determines the presence, threat, extent, and progress of the aerosol cloud. These factors are then telemetrically transmitted by means of alarms and warnings sent to potentially threatened regions. Although Wyatt's system is well-adapted to remote surveillance and he teaches the use of fluorescence to identify biological compounds, his "light scattering" data are adapted to characterizing and counting particles in an aerosol and Wyatt doesn't consider the rapid and automated identification of biological particles.

In U.S. Pat. No. 6,532,067, Chang, et al. describe a method for fluorescence probing of particles flowing in a fluid, including steps of defining a trigger volume in the fluid by intersecting a plurality of substantially orthogonally aimed trigger laser beams, each of a different wavelength, detecting light scattered from the vicinity of the trigger volume by a plurality of particle detectors each sensitive to a wavelength corresponding to the wavelength of a trigger laser beam, probing the particles with a pulsed laser triggered by the particle detectors, collecting fluorescence emitted from the particle in a detection volume and focusing it in a detection region, detecting the fluorescence focused in the detection region. Chang, et al. neither consider nor suggest solutions to the remote automated surveillance problem.

In U.S. Pat. No. 6,613,571, Cordery et al. disclose a method and system for detecting biological and chemical hazards in mail using predetermined descriptions of the hazards sought but they neither consider nor suggest solutions to the remote automated surveillance problem. In U.S. Pat. No. 6,656,253, Willey, et al. disclose a dynamic electrostatic filter apparatus for purifying air using electrically charged liquid droplets but they neither consider nor suggest solutions to the remote automated surveillance problem. In U.S. Pat. No. 6,664,550, Rader et al. describe an aerosol lab-on-a-chip (ALOC) that integrates one or more of a variety of particle collection, classification, concentration (enrichment), an characterization processes onto a single substrate or layered stack of such substrates. By mounting a UV laser diode laser light source on the substrate, or substrates tack, so that it is located down-stream of the sample inlet port and at right angle the sample particle stream, the UV light source can illuminate individual particles in the stream to induce a fluorescence response in those particles having a fluorescent signature such as biological particles, some of said particles. An illuminated particle having a fluorescent signal above a threshold signal may trigger a sorter module that separates that particle from the particle stream. But Cordery et al. consider the process control and particle stream separation problems and neither consider nor suggest solutions to the remote automated surveillance problem.

In view of the recent terrorism-related security requirements mentioned above, there is a clearly-felt need in the art for a robust (military-hardened) miniaturized remote system for the initial detection, localized analysis and reporting of the presence of biohazards. Such a system requires a large number of permanently-deployed remote surveillance stations each of which can operate independently and without human intervention. Such stations must be adapted for accepting updated detection information from a remote control center to permit adaptation to global changes in the threat environment, for example.

These unresolved problems and deficiencies are clearly felt in the art and are solved by this invention in the manner described below.

SUMMARY OF THE INVENTION

This invention solves the above problem by providing a distributed biohazard surveillance system including a plurality of robust miniaturized remote monitoring stations for the detection, localized analysis and reporting of a broad range of biohazards. The remote monitoring station may be adapted to identify many different biological particles and is not limited to particular predetermined biohazard profiles. Each monitoring station is centrally and dynamically reconfigurable and can operate unattended. The distributed system may be used to locate and report unsuspected sources of biohazards and to monitor the localized effects in real-time through cooperation with a centralized data processing facility.

The monitoring station apparatus can also count, categorize (e.g., distinguish biological from non-biological particles), and collect samples of airborne particulate matter for local retrieval and analysis.

In one aspect, the invention is a distributed biological hazard surveillance system including a central processing assembly including means for receiving and transmitting data; and a plurality of detector assemblies disposed throughout a physical region under surveillance for capturing and identifying an airborne particle, each detector assembly including: an intake filter assembly disposed to accept a flow of air containing an airborne particle from the exterior of the detector assembly; a sampling chamber disposed to accept the flow of air and the airborne particle from the filter assembly; a fan disposed to move the air flow and the airborne particle through the intake filter assembly and across the sampling chamber; an optical stage disposed within the sampling chamber, including an electrostatic precipitator disposed to induce in the airborne particle an electrostatic charge sufficient to facilitate capture of the charged airborne particle, an optical assembly disposed to magnify the image of the captured particle, a flash optical source disposed to illuminate the optical stage with an optical pulse, and a digital camera disposed to capture the magnified image of the captured particle during the optical pulse; a processor including memory and processing means together with controlling and processing software for controlling the optical stage, for storing digital image data produced by the digital camera, for analyzing the digital image data to produce analysis data, and for processing and storing the analysis data; and a transmitter coupled to the processor for transmitting the analysis data to the central assembly.

In one embodiment, the invention is a detector assembly for capturing and identifying an airborne particle in a distributed biological hazard surveillance system including an intake filter assembly disposed to accept a flow of air containing an airborne particle from the exterior of the detector assembly; a sampling chamber disposed to accept the flow of air and the airborne particle from the filter assembly; a fan disposed to move the air flow and the airborne particle through the intake filter assembly and across the sampling chamber; an optical stage disposed within the sampling chamber, including an electrostatic precipitator disposed to induce in the airborne particle an electrostatic charge sufficient to facilitate capture of the charged airborne particle, an optical assembly disposed to magnify the image of the captured airborne particle, a flash optical source disposed to illuminate the optical stage with an optical pulse, and a digital camera disposed to capture the magnified image of the captured airborne particle during the optical pulse; a processor including memory and processing means together with controlling and processing software for controlling the optical stage, for storing digital image data produced by the digital camera, for analyzing the digital image data to produce analysis data, and for processing and storing the analysis data; and a transmitter coupled to the processor for transmitting the analysis data to the central processing assembly.

In another aspect, the invention is a machine-implemented method for capturing and identifying an airborne particle including the steps of: (a) accepting a flow of air into a sampling chamber having an optical stage, (b) imposing a first electrical charge on the airborne particle sufficient to facilitate capture of the charged airborne particle in the optical stage, (c) illuminating the optical stage with a brief optical pulse, (d) capturing a microscopic image of the captured particle, (e) generating a digital image data signal representing the microscopic image, (f) generating a digital analysis data signal representing an identification of the captured particle responsive to the application of a plurality of neural network weights to the digital image data signal, and (g) storing the digital analysis data signal in a data store.

In yet another aspect, the invention is a computer program product (CPP) for use in a biological hazard surveillance detector assembly processor that includes a programming system supporting the execution of a method for capturing and identifying an airborne particle, the CPP including a recording medium, means recorded on the recording medium for directing the detector assembly processor to accept a flow of air into a sampling chamber having an optical stage, means recorded on the recording medium for directing the detector assembly processor to impose a first electrical charge on the airborne particle sufficient to facilitate capture of the charged airborne particle in the optical stage, means recorded on the recording medium for directing the detector assembly processor to illuminate the optical stage with a brief optical pulse, means recorded on the recording medium for directing the detector assembly processor to capture a microscopic image of the captured particle, means recorded on the recording medium for directing the detector assembly processor to generate a digital image data signal representing the microscopic image, means recorded on the recording medium for directing the detector assembly processor to generate a digital analysis data signal representing an identification of the captured particle responsive to the application of a plurality of neural network weights to the digital image data signal, and means recorded on the recording medium for directing the detector assembly processor to store the digital analysis data signal in a data store.

The foregoing, together with other objects, features and advantages of this invention, can be better appreciated with reference to the following specification, claims and the accompanying drawing.

BRIEF DESCRIPTION OF THE DRAWINGS

For a more complete understanding of this invention, reference is now made to the following detailed description of the embodiments as illustrated in the accompanying drawing, in which like reference designations represent like features throughout the several views and wherein.

DESCRIPTION OF THE PREFERRED EMBODIMENT

Figure 1:
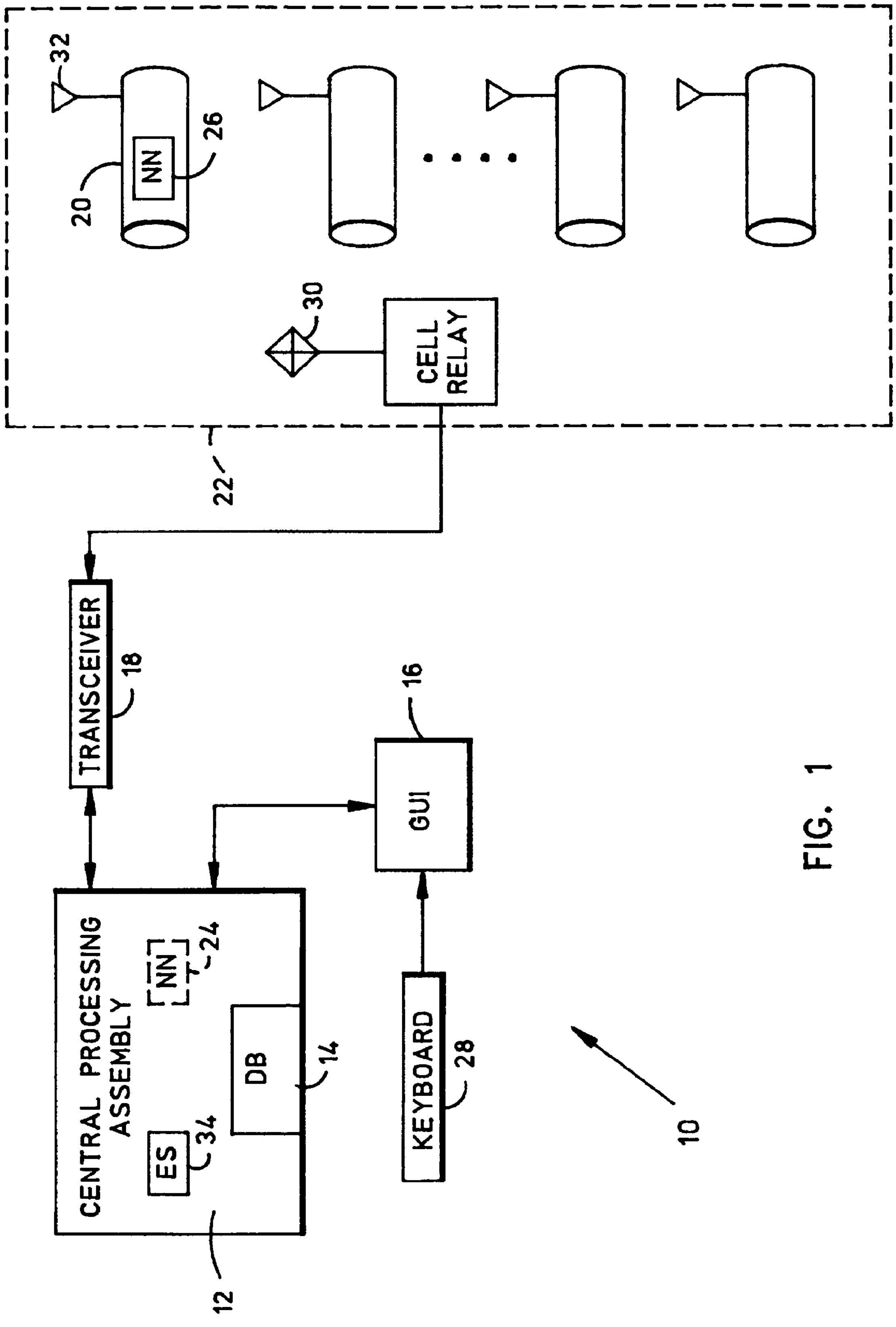
FIG. 1 is a schematic diagram illustrating an exemplary embodiment of the distributed biological hazard surveillance system of this invention.

FIG. 1 is a schematic diagram illustrating an exemplary embodiment of the distributed biological hazard surveillance system 10 of this invention. System 10 includes a central processing assembly 12 including a database 14 coupled to a graphical user interface (GUI) 16 and a transceiver system 18 for communicating with a plurality of detector assemblies, exemplified by the detector assembly 20, that are disposed throughout a physical region 22 under surveillance, which may encompass, for example, a battlefield or a municipality or a portion thereof. Database 14 may include, for example, data representing a plurality of neural network weights for use in a local neural network facility 24 resident in assembly 14 or, alternatively, data representing a plurality of neural network weights adapted for downloading to one or more neural networks exemplified by the neural network integrated circuit (IC) 26 in assembly 20. Such data transfer may be initiated by a user at the keyboard 28 and is facilitated by transceiver 18, which is coupled by some useful means to a local cell phone relay antenna 30 disposed in region 22 to couple with the remote cell phone antenna 32 in the detector assemblies (20). The same facilities may be employed to automatically transfer data in the other direction from assembly 20 in region 22 to central processing assembly 12 for display to the user at GUI 16, for example.

The user (not shown) resides in central processing assembly 12 where the reports from each detector assembly (20) are automatically downloaded and "instructions" may be uploaded to the remote locale as necessary. The images generated at each detector assembly (20) in region 22 may be analyzed locally in neural network IC 26, for example, or centrally in neural network facility 24, before the image identifications are reported to central processing assembly 12. The downloaded identification reports are saved in database 14 where they are periodically "mined" by an expert system 34 to discover pathogen detection pattern anomalies. That is, once the detector assembly images are analyzed to identify pathogens, the overall pathogen detection patterns within region 22 must be analyzed using, for example, a knowledge-based inference engine embodiment, such as a Knowledge Amplifier employing Structured Expert Randomization (KASER) or in any useful expert system embodiment. The KASER is disclosed in the commonly-assigned U.S. patent application Ser. No. 10/206,930 filed on Jul. 24, 2002 and entirely incorporated herein by this reference. Such an analysis can pinpoint the sources and perhaps the likely causes of contamination and also recommend areas for evacuation or other counter-measures. This is possible through the implied fusion of the data with other applicable data such as observed weather patterns, satellite imagery, passenger flight manifests, intelligence reports, etc. Moreover, cognizant authority such as, for example, the Center for Disease Control (CDC), can use the system to identify and control any epidemics. The literature is replete with descriptions, discussions, and many examples of different types of neural networks. The necessary application software may be constructed without undue experimentation by one having access to common knowledge in the software arts.

Figure 2:
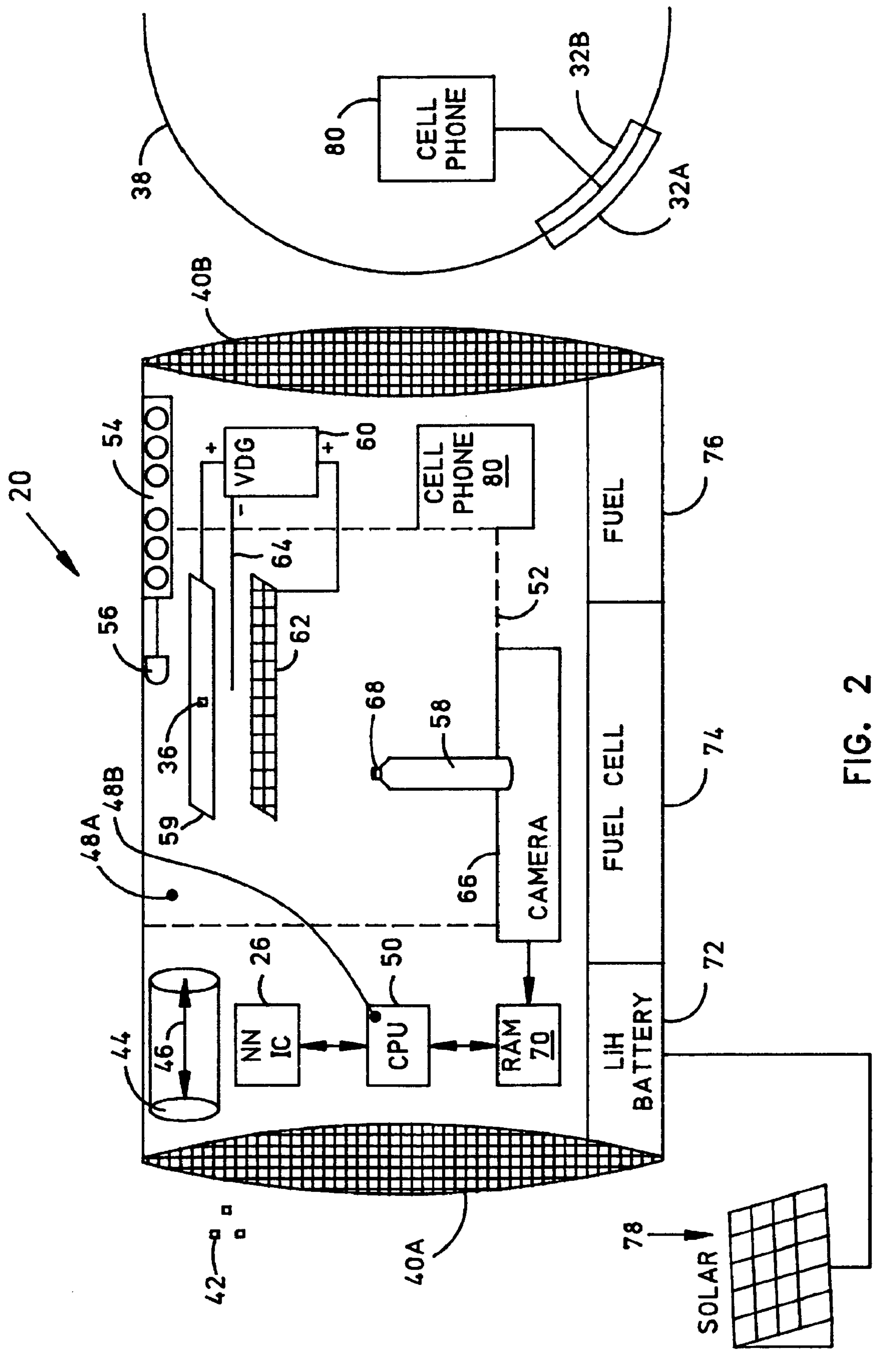
FIG. 2 is a schematic diagram illustrating an exemplary "slide-capture" embodiment of the detector assembly element of the system from FIG. 1.

FIG. 2 is a schematic diagram illustrating a "slide-capture" embodiment of detector assembly 20 from FIG. 1. Assembly 20 is disposed for identifying an airborne particle 36 following its capture on a fixed slide surface and therefore includes several components for that purpose, which may be adapted to fit into a one liter cylindrical container 38 having a total weight less than 2 kg, for example. When deployed into region 22, detector assembly 20 should be disposed under an awning or otherwise protected from precipitation for best performance. Airborne moisture such as fog is not expected to adversely affect operation. Container 38 includes two ends, each of which is fitted with an intake filter assembly 40 including a removable 25 micron filter. Filters 40A–B operate to trap particulate matter, such as the particle 42, that is too large to be of interest, thereby preventing the premature fouling of the internal detecting mechanism. A simple fan 44 creates a pressure differential across filters 40A–B, which effectively circulates outside air across the internal detecting mechanism. Reversing the polarity of power (not shown) to fan 44 operates to reverse the airflow direction shown by the arrow 46, thereby flushing filters 40A–B sufficiently to extend the expected operating interval between servicing visits. Fan 44 is preferably disposed on compliant mountings (not shown) such as silicon rubber mounts, for example, to dampen the transmission of any fan motor vibration to the internal detecting mechanism. A pair of thermistors 48A–B is disposed to measure the temperature differential between the processor 50 and the ambient internal container. If fan 44 fails or if either filter 40A–B clogs, the ambient temperature may rises and processor 50 may overheat. Should this occur, the ratio of processor temperature to ambient temperature as measured by at thermistors 48A–B rises from about unity to some predetermined bound. This thermal ratio may be computed by processor 50, for example. When this thermal ratio exceeds some predetermined bound, then processor 50 causes the transmission to central processing assembly 12 of a thermal overload alert indicating a probable clogged filter or defective fan motor, resulting in a shutdown of all power to detector assembly 20. Alternatively, the rotary direction of fan 44 may be reversed to reverse the air flow indicated by arrow 46 and the planned power interruption deferred for a predetermined interval to permit any improved air flow to reduce the thermal ratio below the cutoff threshold. Air flow reversal should blow out the blockage to some extent.

Several additional components are disposed to create an optic stage 52. These include a capacitor bank 54, a flash diode 56, and a quartz optical microscope 58, which are separately illustrated for expository purposes but are preferably embodied monolithically as optic stage 52 shown in more detail in FIGS. 3–4. A slightly-heated particle such as particle 36 is blown across optic stage 52 wherein it is electrostatically precipitated onto the slide 59 ("slide capture") by means of an electrostatic precipitator formed by the Van de Graaff generator 60, the attractor grid 62 and one or more ion emitters exemplified by the platinum wire tip 64. Flash diode 56 produces a burst of short-wave ultraviolet (UV) light, which "freezes the frame" to permit image capture by a digital camera 66. Microscope 58 is fitted with the quartz lenses 68 selected to transmit UV wavelengths and to provide the magnification desired for identification of the particles sought. Lenses 68 may be automatically interchangeable but this is not required for acceptable operation. A digital zoom feature may also be included in digital camera 66 to help adjust image magnification but it is not required for acceptable operation. The optical image from microscope 58 is captured by digital camera 66 and stored in the random access memory (RAM) 70. Processor 50 operates in cooperation with neural network IC 26 to identify and categorize particle 36 and to compute and accumulate statistics representing the historical detection class densities, for example. Processor 50, digital camera 66 and other sensitive electronic components in the vicinity of optic stage 52 must be properly shielded and grounded to prevent damage from the static charges induced by Van de Graaff generator 60.

Neural IC 26 may be embodied, for example, as a neural network whose number of fundamental memories is expected to increase supra-linearly with scale. Neural network IC 26 may be integrated with processor 50 or implemented as a separate IC as shown, for example. Neural network IC 26 should identify sharper class distinctions and be more tolerant of the orientation problem than are conventional neural network architectures. Such a capability could usefully categorize a particle having characteristics of bacteria A and bacteria B as being of type A, type B, or unknown. That is, the provision for feedback in such a neural network implies a better capability for discriminating among particles that may otherwise appear similar.

The functions of neural IC 26 may be remotely disposed at central processing assembly 12 instead of locally by moving all processing to the back-end of the system architecture, but this is not preferred because of the cellular transmission time required to accommodate reductions in distributed processing and localized decision making. Neural IC 26 may be embodied as any useful neural network; e.g., the weightless Zero Instruction Set Computer (ZISC) pattern-recognition chip produced by Silicon Recognition, Inc. If neural IC 16 is embodied as a weighted neural network, then hidden-layer technology is required (e.g., a perceptron is not recommended). This is necessary to enable system 10 to distinguish concave from convex spirals, for example. The choice between weighted and weightless neural networks embodiments may be accomplished without undue experimentation and either type of network can be generally useful, however. Neural network 26 is trained in the laboratory; e.g., by using Kohonen learning or the slower back-propagation model for the weighted network. With sufficient fundamental memory, sufficient training and sufficient detection time, particulate orientation and partial occlusion should not prevent the necessary particle assay.

There are several alternatives illustrated for powering detector assembly 20. A rechargeable lithium-metal hydride battery 72 is alone sufficient to power assembly 20 continuously for few days, but additional power is required to achieve the preferred one-month stand-alone capability. Alternatively, a shielded and grounded methanol-based micro fuel cell 74 of the type currently used for powering cell phones and laptop computers should be able to power the system continuously for up to a month; perhaps with an external methanol bottle (not shown) to supplement the internal fuel store 76. A silicon solar cell array 78 is preferred to charge battery 70 or to electrolyze water to provide fuel to fuel cell 74. Such an arrangement should permit assembly 20 to remain powered and operational at night or on heavily overcast days. The necessary size of array 78 depends on the location, temperature (solar cells are more efficient at lower temperatures), time-of-year, and maximum acceptable downtime. Smaller solar arrays are suitable for the cooler sunny regions. Many such useful arrays are readily available in the art and are commonly used for powering emergency roadside phones in remote areas, for example. Of course, where standard alternating current (AC) power is available, detector assembly 20 may be powered by means of any suitable AC power supply adapter, for example.

The cell phone 80 communicates through cell antenna 32 with cell phone relay antenna 30 (FIG. 1) disposed in region 22. A thin-client Java-based operating system of the type used to control cell-phone operations is sufficient for controlling the operation of cell phone 80. All communication protocols can be realized without undue experimentation by practitioners having access to common knowledge and standard practices in the field of communication architecture. Digital camera 66 and RAM 70 transceive through cell phone 80, which preferably uses an outer gold-plated conformal embodiment (32A) of antenna 32 that conforms to cylindrical container 38 and also reflects any scattered infrared (IR) radiation to reduce unit heating from incident sunshine. Preferably, assembly 20 should be configured to operate at temperatures from −20 to +50 degrees Celsius. The inner gold-plated surface (32B) of antenna 32 serves as a front-surface mirror to diffuse and increase the intensity of the short-wave UV flash provided by flash diode 56. When digital camera 66 is embodied as a charge-coupled device (CCD) camera, the CCD element's well-known sensitivity to high-energy short-wave UV light permits practical use of microsecond flash periods.

Another feature of the system of this invention is that cell phone 80 can be used to both remotely download images and to upload new neural network weights (or data vectors for weightless networks such as the ZISC mentioned above). Assembly 20 may update its particulate detection capability on a regular or irregular basis. This feature permits adapting system 10 to detect new biological threats as more assemblies 20 are deployed remotely.

To conserve power, fan 44 can be operated through timer intervals or remotely by way of cell phone 80, or through the setting of the timer intervals by means of cell phone 80. With extensive conservation, rechargeable lithium-metal hydride battery 72 may be sufficient to power detector assembly 20 intermittently over the preferred one-month operating period. As fan 44 is operated less frequently, the time interval between servicing filters 40A–B is increased because of reduced airflow. Also, the time interval between servicing grid 62 is similarly increased because optic stage 52 is powered down when fan 44 is powered down.

As described herein, detector assembly 20 can operate as part of a robust, military-hardened miniaturized system for the detection, localized analysis and transmission of information on the presence of biohazards. Detector assembly 20 can count, categorize, distinguish biological from non-biological particles, and collect airborne particulate matter on grid 62 as well as in filters 40A–B. In addition, detector assembly 20 is centrally and dynamically reconfigurable and can be adapted to operate unattended for periods of at least one month between maintenance cycles and in temperatures from −20 to 50 degrees Celsius, for example. A plurality of detector assemblies 20 can be distributed to pinpoint sources of biohazards and to suppress their deleterious effects through integration with centralized processing assembly 12 in a distributed biological hazard surveillance system 10.

Figure 3:
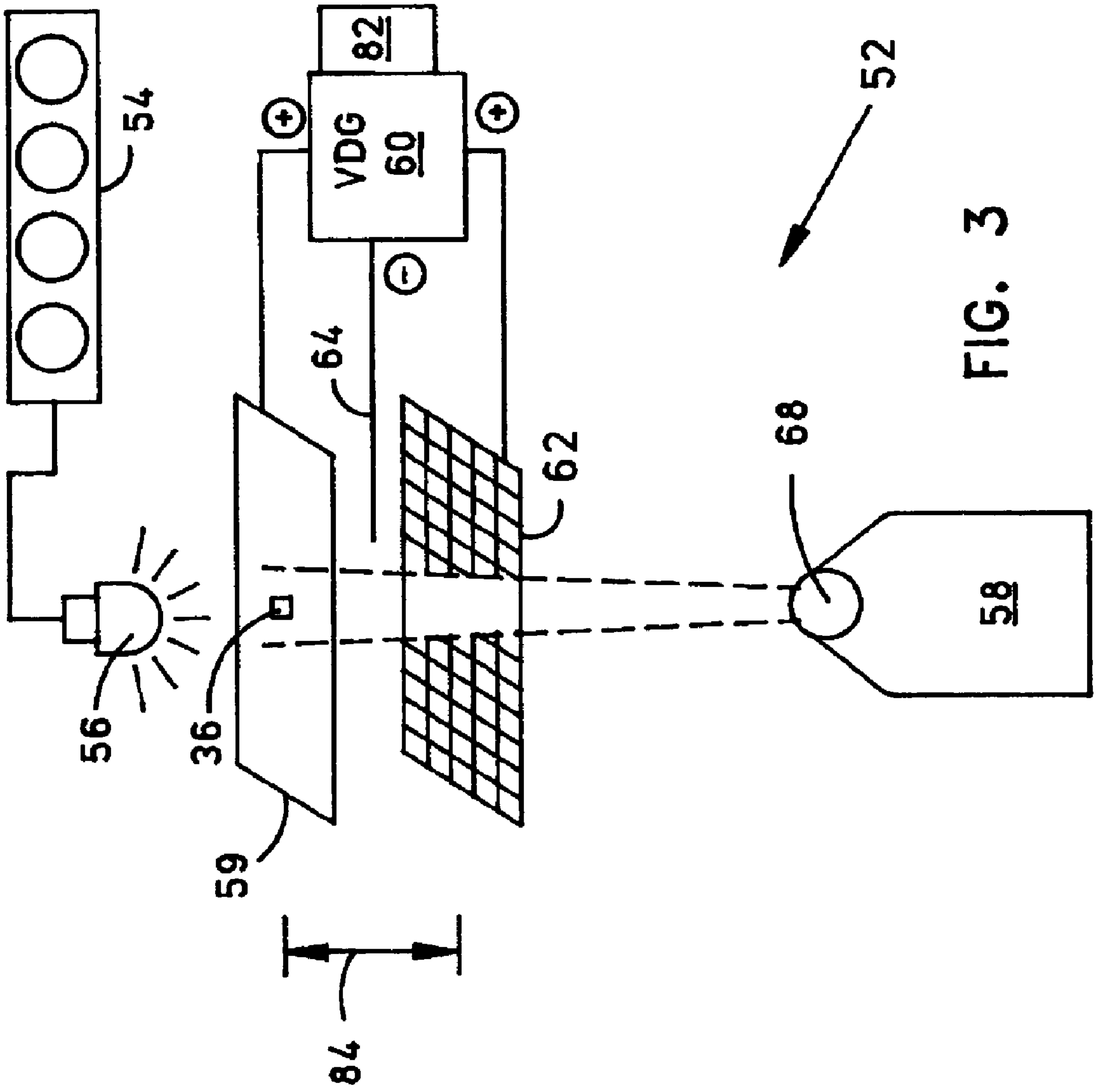
FIG. 3 is a schematic diagram illustrating the exemplary "slide-capture" embodiment of the optical stage element of the assembly from FIG. 2.

FIG. 3 is a schematic diagram illustrating in more detail the exemplary "slide-capture" embodiment of optical stage 52 from FIG. 2. Capacitor bank 54 supplies energy through a power transistor (not shown) to short-wave UV flash diode 56. The duration of this flash should be no more than a few hundred microseconds to avoid pushing particle 36 off of slide 59 by some combination of localized heating, mechanical and UV-electrostatic processes. Slide 59 should be made of UV-transparent quartz instead of glass, which does not generally transmit short-wave UV. This is necessary to optimize the resolution of microscope 58. Slide 59 is lightly aluminized on the front surface to allow it to conduct the high voltage charge while transmitting light. That is, the aluminized coating reflects some of the incident light, thereby operating as a semi-transparent mirror. The coating also functions to distribute the high-voltage electric charge while remaining mostly transparent to the short-wave UV from flash diode 56.

Van de Graaff generator 60 supplies the charge to the ion emitters exemplified by platinum wire tip 64. Van de Graaff generator 60 is embodied preferably as a well-known beltless cigar-shaped embodiment that may be powered from an automobile cigarette lighter socket for use as a negative ion supplier in the automobile, for example. A set of power transistors and a capacitor-based timer 82 is provided to alternate the charge polarity to slide 59, grid 62 and one or more ion emitters exemplified by platinum wire tip 64. The rate at which the charge polarity may be alternated is limited by the parasitic capacitance of slide 59, but the charge should be alternated rapidly enough to avoid building up an obfuscating deposit on slide 59. The proper charge polarity alternation rate can be determined using dry air at standard temperature and pressure (STP) without undue experimentation. Capacitor bank 54 is disposed so that its time constant matches twice the desired alternation period.

The distance 84 between slide 59 and grid 62 should be set to 2.828 (i.e., two times the square root of two, as the charge density is inversely proportional to the square of the distance) times the maximum polarized arc distance at STP. The diameter of platinum wire tip 64 may be assumed to be negligible here. This does not pose a problem for the focal length of the microscope 58 because the distance between slide 59 and the platinum ion emitters exemplified by platinum wire tip 64 is mechanically variable. As the ion emitters exemplified by platinum wire tip 64 are moved closer to slide 59, more particulate matter is deposited on slide 59 instead of grid 62, up to the maximum arc distance. This distance need not be automatically adjusted but rather should be set manually to obtain an acceptable average particle density for microscopic examination in the particular locale and ambient conditions.

In operation, capacitor bank 54 is charged, while the ion emitters exemplified by platinum wire tip 64 are charged negatively (i.e., by circuit 82) and slide 59 and grid 62 are held to ground or the opposite positive polarity. This causes particulate matter to deposit on slide 59 and grid 62 in proportion to the relative distances separating them from the ion emitters exemplified by platinum wire tip 64. Next, flash diode 56 is fired by circuitry (not shown) contained in capacitor bank 54. Microscope 58 then relays the particulate image to digital camera 66. Then, capacitor bank 54 begins to recharge while slide 59 is charged negatively while the platinum ion emitters exemplified by platinum wire tip 64 and grid 62 are held to ground or the opposite positive polarity. Any particles on slide 59 then take on the negative charge from slide 59 and are immediately repelled to grid 62 and, to a lesser extent, to the ion emitters exemplified by platinum wire tip 64. This disposition of the particles after imaging can be readily appreciated as inconsequential for the next imaging cycle. A few particles may be imaged more than once in different positions and orientations, but this is not disadvantageous and may perhaps be useful for selecting particle orientation and for training the neural network, for example. Over several cycles, new particles should in fact be sampled. Grid 62 may be periodically cleaned and various biological assays performed on the matter removed therefrom. Such assays may include reviews for any viral particles too small for optical detection. Because the peculiar effects that viral particles display after having invaded a bacterial host may be optically detectable, an embodiment of optic stage 52 may be adapted for the indirect detection of a limited number of active viral particles. A similar, but more complex system capable of direct viral detection may be implemented by replacing optical microscopic 58 with an electron microscopic assembly, but only with significant increases in cost and complexity.

Figure 4:
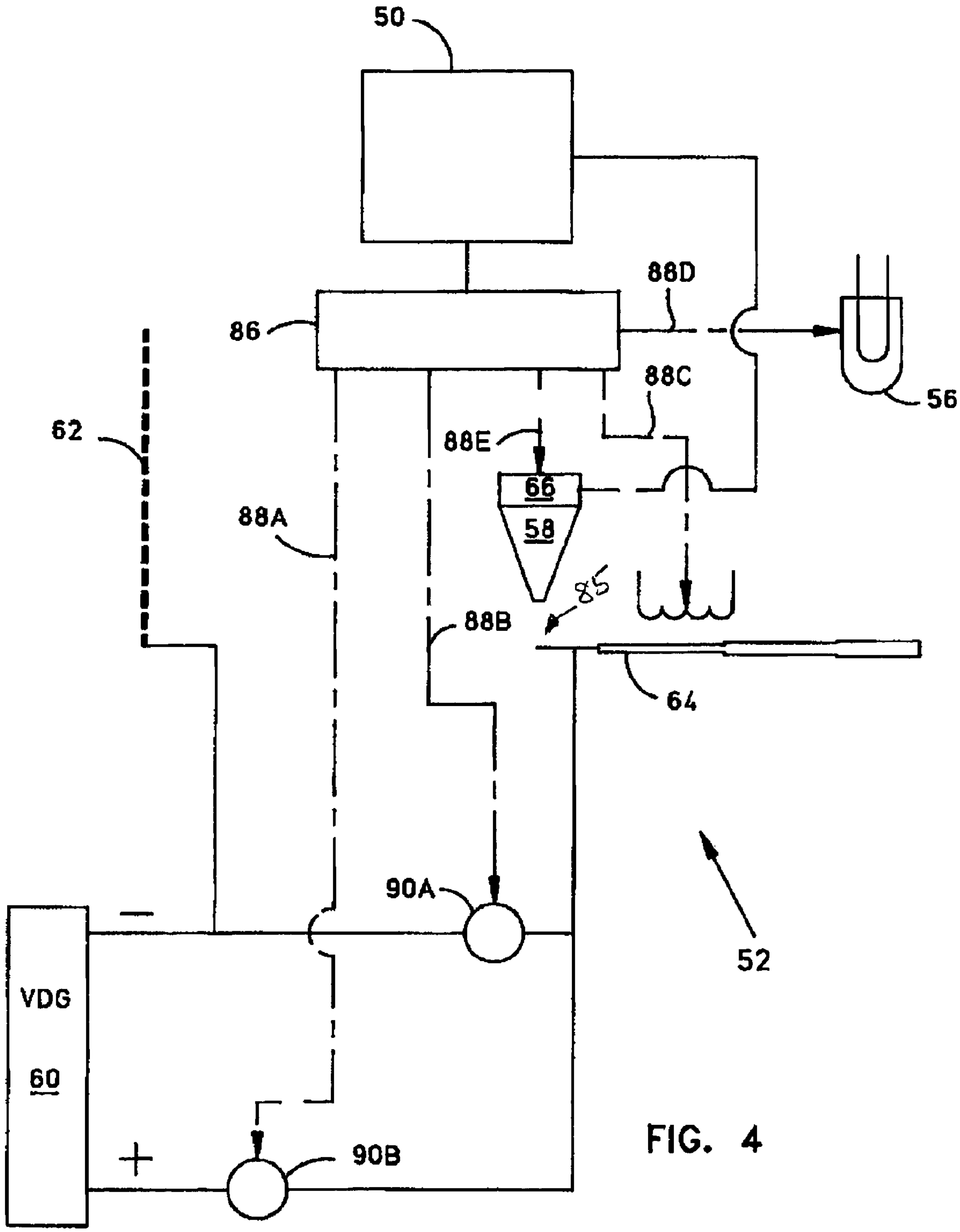
FIG. 4 is a schematic diagram illustrating an exemplary "vortex-capture" embodiment of the optical stage element of the system from FIG. 1.

FIG. 4 is a schematic diagram illustrating an exemplary "vortex-capture" embodiment of detector assembly 20 from FIG. 1. In this embodiment of optical stage 52, the incoming air is charged by running through screen mesh 62 linked to Van de Graaff generator 60. By charging the ion emitter embodied as platinum wire tip 64 with the opposite voltage, the particles are attracted thereto, acquire the same charge and then are quickly repelled therefrom. A controlled change of the charge imposed on platinum wire tip 64 can be used to affect the motion of the charged particle. Because the particles are quite small in size and light in weight, the attraction and extraction process is very fast and operates to create a "vortex" region 85 around platinum wire tip 64, the features of which are not precisely knowable. Slide 59 (FIG. 3) is not provided and is not required because the charged particle is briefly "captured" in vortex region 85 by virtue of the charges applied to the elements of optical stage 52. Accurate and precise flash timing is crucial to the successful imaging of the captured particle (not shown), which is only briefly captured in vortex region 85. Flash diode 56 must be driven at 25 microseconds to enable camera 66 to statistically succeed in capturing an image of the particulate matter in vortex region 85. However, at 25 microseconds per image, while camera 66 does succeed in "stopping" the particle image in vortex region 85, it also produces an unnecessarily large number of images when the attraction speed happens to be substantially slower than 25 microseconds. This disadvantageously increases image transmission and processing time and requires more image data storage space. The addition of a suitable padding interval between subsequent images may reduce prolixity but may interfere with the capture of the desired particle image.

The "vortex-capture" embodiment of optical stage 52 illustrated in FIG. 4 resolves the image prolixity problem as follows. A main controller 86 embodied as a single-board computer sends the control messages 88A–E to camera 66, flash diode 56 and the relays 90A–B in the charging circuit from Van de Graaff generator 60 as shown. Relays 90A–B are first set by controller 86 to charge grid 62 and platinum wire tip 64 with opposing voltages. This operates to charge any particles floating in the incoming air as they flow through grid 62 so they are attracted to vortex 85 around platinum wire tip 64. Then, after some delay but before the particles are extracted as they attain the voltages of platinum wire tip 64, controller 86 activates camera 66 and flash diode 56 to acquire the particle image. By means of a simple software program for the controller, the activating timing for each component can be set properly as follows.

Except for the discrete drive time imposed by the hardware (e.g., camera 66) the software program can adjust the activating time almost continuously. Therefore, supposing that the charging speed is constant, the activating time for the camera and flash can be varied until the sample images are satisfactory to experimentally identify a satisfactory activation timing scheme, without undue experimentation. This embodiment permits the particles to be captured at the right time without unnecessary increases to the computational cost and storage space. It is advantageously much easier to adjust the software program timing codes than to modify the hardware arrangements when adapting assembly 20 for different environments and requirements.

Figure 5:
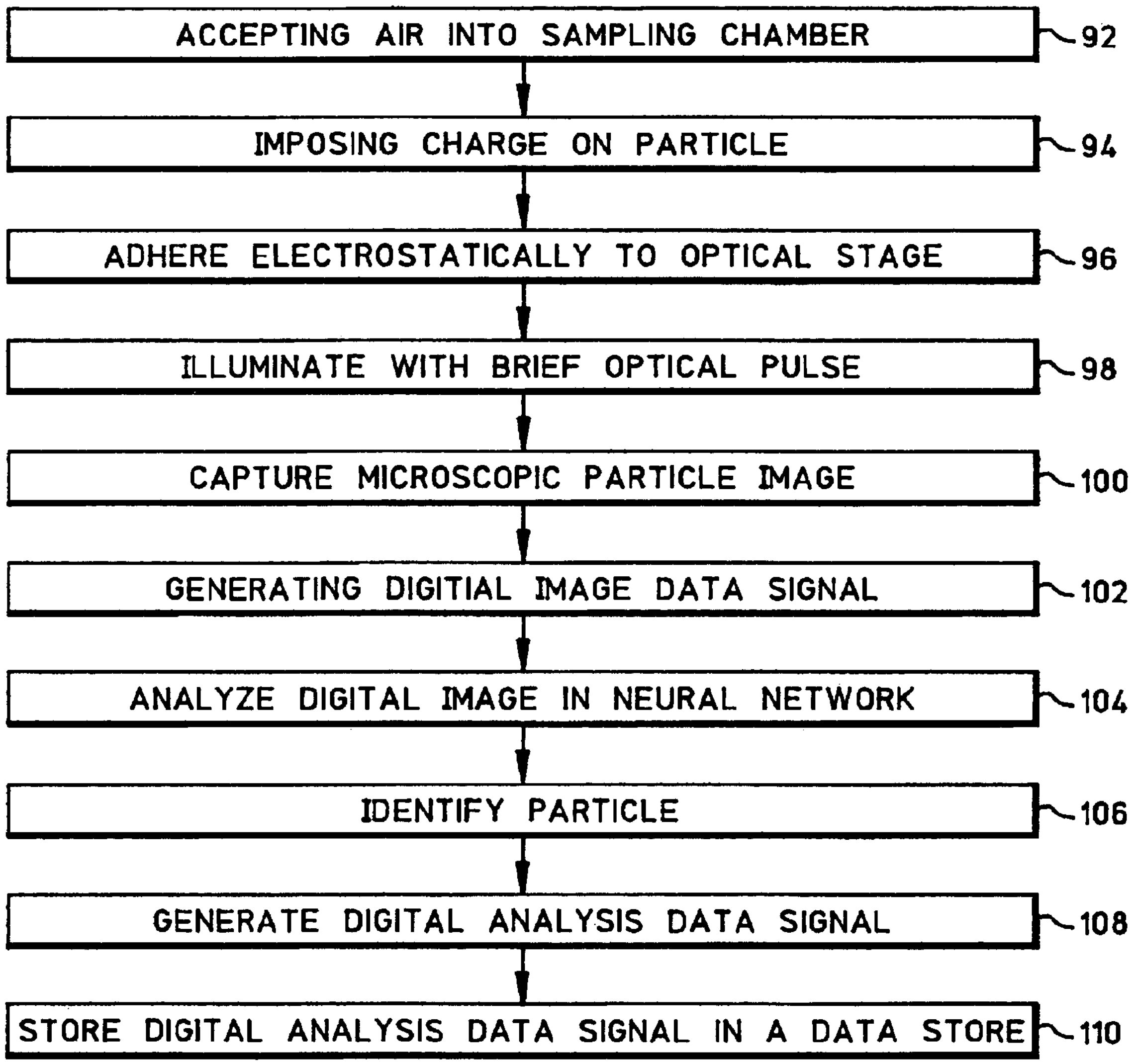
FIG. 5 is a block diagram of a flow chart illustrating an exemplary embodiment of the particulate surveillance method of this invention.

FIG. 5 is a block diagram of a flow chart illustrating an exemplary embodiment of the particulate surveillance method of this invention. In the first step 92, a fan is turned to cause air containing airborne particles to be drawn into a sampling chamber. In the next step 94, at least one airborne particle is subjected to an electric charge by an ionizing means, which causes the charged particle to adhere electrostatically to a viewing surface in the optical stage in the step 96. In the next step 98, the optical stage is illuminated with an optical pulse that is sufficiently brief to freeze all apparent motion of the adhering particle. In the step 100, an image of the briefly illuminated particle is captured in a digital image sensing device and, in the next step 102, converted to a digital image signal and stored in a digital data store.

The stored image signal is then transferred to a neural network for analysis and identification in the step 104. This analysis may rely on a number of neural network weights acquired or evolved through a training program or introduced from some outside data store, for example. The result is the determination of a particle identification in the step 106, which is used to generate a digital analysis data signal in the step 108 for use in a particle detection report. Finally, the digital analysis data signal is stored in a data store in the final step 110, where it remains available for transmission to a central analysis facility or for local development of detection statistics and other data mining operations.

Figure 6:
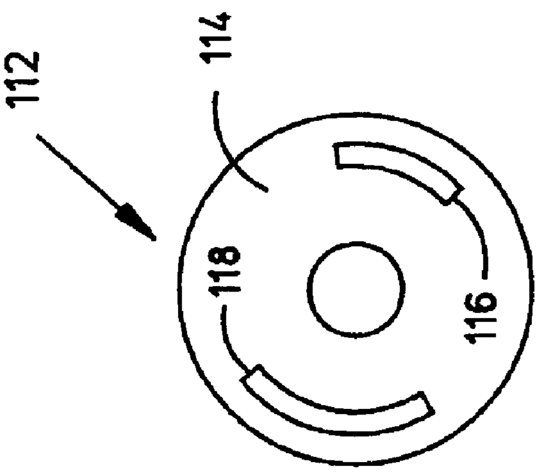
FIG. 6 is a schematic diagram illustrating an exemplary embodiment of the computer program product (CPP) of this invention.

FIG. 6 is a schematic diagram illustrating a Compact Disk Read-Only Memory (CDROM) embodiment 112 of the computer program product (CPP) of this invention. CDROM 112 includes a recording medium 114 for storing computer program instructions in binary or digital form for directing a computer processor to perform certain predetermined steps. For example, the computer program instructions 116 and 118 are stored on storage medium 114 of CDROM 112 for retrieval by a suitable computer processor in the well-known manner. Of course, the CPP of this invention may also be embodied as, for example, a non-volatile RAM or a Digital Versatile Disk (DVD) or any other useful embodiment.

Clearly, other embodiments and modifications of this invention may occur readily to those of ordinary skill in the art in view of these teachings. Therefore, this invention is to be limited only by the following claims, which include all such embodiments and modifications when viewed in conjunction with the above specification and accompanying drawing.

It will be understood that many additional changes in the details, materials, steps and arrangement of parts, which have been herein described and illustrated to explain the nature of the invention, may be made by those skilled in the art within the principal and scope of the invention as expressed in the appended claims.

We claim:

1. A distributed biological hazard surveillance system comprising:

a central processing assembly including means for receiving and transmitting data; and a plurality of detector assemblies disposed throughout a physical region under surveillance for capturing and identifying an airborne particle, each detector assembly including:

an intake filter assembly disposed to accept a flow of air containing an airborne particle from the exterior of the detector assembly;

a sampling chamber disposed to accept the flow of air and the airborne particle from the filter assembly;

a fan disposed to move the air flow and the airborne particle through the intake filter assembly and across the sampling chamber;

an optical stage disposed within the sampling chamber, including an electrostatic precipitator disposed to induce in the airborne particle an electrostatic charge sufficient to facilitate capture of the charged airborne particle, an optical assembly disposed to magnify the image of the captured particle, a flash optical source disposed to illuminate the optical stage with an optical pulse, a digital camera disposed to capture the magnified image of the captured particle during the optical pulse, and a synchronizing controller coupled to the electrostatic precipitator for coordinating electrostatic precipitator operation with the operation of the digital camera and flash optical source to capture the charged airborne particle in a vortex and to obtain the magnified image thereof;

a processor including memory and processing means together with controlling and processing software for controlling the optical stage, for storing digital image data produced by the digital camera, for analyzing the digital image data to produce analysis data, and for processing and storing the analysis data; and a transmitter coupled to the processor for transmitting the analysis data to the central assembly.

2. The system of claim 1 further comprising:

an optical stage examination surface disposed within the optical stage to capture the charged airborne particle.

3. The system of claim 2 further comprising:

charge reversing means coupled to the electrostatic precipitator for inducing in the captured particle an electrostatic charge sufficient to repel the captured particle from the optical stage examination surface.

4. The system of claim 1 further comprising:

a neural network disposed to accept the digital image data and to produce the analysis data representing an identification of the captured particle.

5. The system of claim 4 further comprising:

a receiver coupled to the processor for receiving data representing a plurality of neural network weights.

6. The system of claim 1 further comprising:

in the central processing assembly, a graphical user interface (GUI) disposed to accept instructions from a system user.

7. The system of claim 6 further comprising:

a separate telemetric module disposed in communication with the central processing assembly to transmit data representing appropriate warnings of imminent threat to the physical region under surveillance, responsive to the analysis data.

8. The system of claim 1 further comprising:

a separate telemetric module disposed in communication with the central processing assembly to transmit data representing appropriate warnings of imminent threat to the physical region under surveillance, responsive to the analysis data.

9. In a distributed biological hazard surveillance system including a central processing assembly including means for receiving and transmitting data to a plurality of such detector assemblies disposed throughout a physical region under surveillance, a detector assembly for capturing and identifying an airborne particle, the detector assembly comprising:

an intake filter assembly disposed to accept a flow of air containing an airborne particle from the exterior of the detector assembly;

a sampling chamber disposed to accept the flow of air and the airborne particle from the filter assembly;

a fan disposed to move the air flow and the airborne particle through the intake filter assembly and across the sampling chamber;

an optical stage disposed within the sampling chamber, including an electrostatic precipitator disposed to induce in the airborne particle an electrostatic charge sufficient to facilitate capture of the charged airborne particle, an optical assembly disposed to magnify the image of the captured airborne particle, a flash optical source disposed to illuminate the optical stage with an optical pulse, a digital camera disposed to capture the magnified image of the captured airborne particle during the optical pulse, and a synchronizing controller coupled to the electrostatic precipitator for coordinating electrostatic precipitator operation with the operation of the digital camera and flash optical source to capture the charged airborne particle in a vortex before capturing the magnified image;

a processor including memory and processing means together with controlling and processing software for controlling the optical stage, for storing digital image data produced by the digital camera, for analyzing the digital image data to produce analysis data, and for processing and storing the analysis data; and a transmitter coupled to the processor for transmitting the analysis data to the central processing assembly.

10. The assembly of claim 9 further comprising:

an optical stage examination surface disposed within the optical stage to capture the charged airborne particle.

11. The assembly of claim 10 further comprising:

charge reversing means coupled to the electrostatic precipitator for inducing in the captured particle an electrostatic charge sufficient to repel the captured particle from the optical stage examination surface.

12. The system of claim 9 further comprising:

a neural network disposed to accept the digital image data and to produce the analysis data representing an identification of the captured particle.

13. The system of claim 9 further comprising:

a separate telemetric module disposed in communication with the central processing assembly to transmit data representing appropriate warnings of imminent threat to the physical region under surveillance, responsive to the analysis data.

* * * * *